United States Patent [19]

Kummer et al.

[11] Patent Number: 4,523,027
[45] Date of Patent: Jun. 11, 1985

[54] PURIFICATION OF CARBOXYLATES CONTAINING ALDEHYDES, ACETALS AND/OR UNSATURATED COMPOUNDS

[75] Inventors: Rudolf Kummer, Frankenthal; Heinz-Walter Schneider, Ludwigshafen; Volker Taglieber, Eppelheim; Franz-Josef Weiss, Neuhofen, all of Fed. Rep. of Germany

[73] Assignee: BASF Aktiengesellschaft, Fed. Rep. of Germany

[21] Appl. No.: 518,006

[22] Filed: Jul. 28, 1983

[30] Foreign Application Priority Data

Jul. 30, 1982 [DE] Fed. Rep. of Germany ....... 3228500

[51] Int. Cl.³ .............................................. C07C 67/56
[52] U.S. Cl. ...................................... 560/191; 203/32; 203/91; 260/410.9 R; 260/420; 502/11; 502/74; 560/1; 560/114; 560/122; 560/127; 560/190; 560/204
[58] Field of Search .................... 502/11, 74; 260/410.9 R, 420; 560/1, 114, 122, 127, 190, 191, 204; 203/32, 91

[56] References Cited

U.S. PATENT DOCUMENTS

| | | | |
|---|---|---|---|
| 2,043,688 | 6/1936 | Woodhouse | 560/191 X |
| 2,801,263 | 7/1957 | Hasek et al. | 560/204 |
| 3,176,028 | 3/1965 | Cross | 260/397.1 |
| 4,189,599 | 2/1980 | Kesling et al. | 560/190 |
| 4,331,812 | 5/1982 | Smiley | 560/191 |

Primary Examiner—Natalie Trousof
Assistant Examiner—Vera C. Clarke
Attorney, Agent, or Firm—Keil & Weinkauf

[57] ABSTRACT

Carboxylates which contain aldehydes, acetals and/or unsaturated compounds and are obtained by reacting an olefinically unsaturated compound with carbon monoxide and an alkanol are purified by a process wherein the said carboxylates are treated with hydrogen at elevated temperatures in the presence of an acidic ion exchanger or zeolite doped with one or more metals of group VIII of the periodic table, and the resulting low and/or high boilers are separated off by distillation.

5 Claims, No Drawings

PURIFICATION OF CARBOXYLATES CONTAINING ALDEHYDES, ACETALS AND/OR UNSATURATED COMPOUNDS

The carbonylation of olefins, i.e. the reaction of, for example, ethylene, propylene or butylene with carbon monoxide and an alkanol in the presence of a carbonyl complex of a metal of group VIII of the periodic table, is used for the large-scale industrial production of carboxylates. If the starting material used is a diolefin, e.g. 1,3-butadiene, the reaction proceeds via the intermediate pentenoate to give dimethyl adipate, which is a useful starting material for the production of textile raw materials. Since carbon monoxide frequently contains a small amount of hydrogen or reacts with entrained water to from hydrogen, the carbonylation reaction is accompanied by a hydroformylation reaction. This gives aldehydes, which react with any alkanols present to give acetals. Moreover, depending on the synthesis, unsaturated ketones, e.g. tridecenones, and butenedicarboxylates are obtained as by-products in low concentrations. When the boiling points of the acetals, aldehydes, unsaturated ketones or butenedicarboxylates are very close to those of the resulting ester, a very technically complicated procedure is required in order to separate off these undesirable by-products by distillation. In the production of adipates, it is particularly important to separate off aldehydes, acetals and unsaturated compounds; if this is not done, the adipic acid prepared from these adipates is not very suitable for the production of textile-grade polymers. Moreover, when even small amounts of aldehydes, acetals and unsaturated compounds are present, the resulting products exhibit undesirable discolorations.

It is an object of the present invention to provide a process which makes it possible to remove acetals, aldehydes and/or unsaturated compounds from carboxylates by a simple procedure.

We have found that this object is achieved by a process for purifying carboxylates which contain aldehydes, acetals and/or unsaturated compounds and are obtained by reacting an olefinically unsaturated compound with carbon monoxide and an alkanol, wherein the said carboxylates are treated with hydrogen at elevated temperatures in the presence of an acidic ion exchanger or zeolite doped with one or more metals of group VIII of the periodic table, and the resulting low and/or high boilers are separated off by distillation.

The novel process has the advantage that the esters can be freed from the contaminating aldehydes, acetals and/or unsaturated compounds by a simple procedure, which replaces the very expensive multi-stage purification process otherwise required. The carboxylates purified by the novel process are very pure since quantitative removal of the acetals, the aldehydes and the unsaturated compounds is effected, and the butenedicarboxylate present is even converted to a useful product.

The general inventive concept is as follows: the acetals which have boiling points close to that of the carboxylate are converted catalytically to vinyl ethers, which are hydrogenated to low-boiling esters and separated off as such, or the aldehydes and acetals are converted to high boilers by an aldol reaction, and these are separated off. Butenedicarboxylates are converted to useful products, i.e. adipates, by hydrogenation. The unsaturated ketones are converted to saturated ketones, which can be separated off by distillation.

Preferred carboxylates are obtained by carbonylation of $C_2$-$C_{12}$-monoolefins, $C_4$-$C_{12}$-diolefins, $C_5$-$C_{12}$-cycloalkenes or $C_1$-$C_8$-alkyl $C_3$-$C_{12}$-alkenemonocarboxylates. The carbonylation is carried out by a conventional method, by reaction with carbon monoxide and a $C_1$-$C_8$-alkanol, in particular a $C_1$-$C_4$-alkanol, for example at from 100° to 200° C. and under from 50 to 1000 bar in the presence of a carbonyl complex of a metal of group VIII of the periodic table, in particular of a cobalt or rhodium carbonyl complex. This gives $C_3$-$C_{13}$-monocarboxylates of alkanols of 1 to 8 carbon atoms, $C_6$-$C_{14}$-dicarboxylates of alkanols of 1 to 8 carbon atoms or cycloalkanecarboxylates having 5 to 12 carbon atoms in the ring. Saturated mono- and dicarboxylates having the stated number of carbon atoms are particularly preferred. Esters prepared in this manner contain, as by-products, aldehydes and acetals, the aldehyde component having the same number of carbon atoms as the corresponding carboxylic acid. Moreover, the acetals contain radicals corresponding to the alkanols used. Other by-products are unsaturated ketones or unsaturated dicarboxylates, depending on the type of starting material used. The content of aldehydes and acetals is, for example, from 0.1 to 15% by weight. Suitable processes are described in, for example, U.S. Pat. No. 3,176,028 and German Laid-Open Application DOS No. 1,618,156.

$C_1$-$C_4$-alkyl adipates have become particularly important industrially; they are prepared by carbonylation of butadiene or a $C_1$-$C_4$-alkyl pentenoate with carbon monoxide and a $C_1$-$C_4$-alkanol. A typical mixture contains, in addition to adipic acid, for example from 9 to 14% by weight of methylglutarates, from 2 to 5% by weight of ethylsuccinates, from 0.1 to 0.3% by weight of 5-formylvalerates, from 0.2 to 0.5% by weight of 6,6-dimethoxycaproates, from 0.03 to 0.1% by weight of butenedicarboxylates and from 0.005 to 0.02% by weight of tridecenones. Suitable processes are described in, for example, U.S. Pat. No. 2,801,263 and German Pat. No. 2,713,195.

Suitable catalysts are acidic ion exchangers and zeolites which are doped with one or more metals of group VIII of the periodic table. Examples of suitable metals are cobalt, nickel, palladium and platinum, particularly preferred metals being palladium and platinum, in particular palladium. Advantageously, the acidic ion exchangers and zeolites contain from 0.5 to 5% by weight of the stated metals. Examples of suitable zeolites are A, X and Y zeolites, as well as natural zeolites, such as fanjasites and nordenites. Strongly acidic ion exchangers (crosslinked polystyrene containing sulfonic acid groups) are particularly preferred.

The catalysts according to the invention are prepared, for example, as follows: the acidic ion exchanger is suspended in water, a dilute palladium nitrate solution containing the calculated amount of palladium is added to the stirred suspension, and the product is filtered off, washed and isolated. When used in a batchwise procedure, the catalyst is washed water-free with methanol in a separate step; when used in a continuously operated reactor, the drying is advantageously carried out in the reactor itself.

At the acidic centers of the catalyst, the most important impurity in terms of amount, i.e. the acetal (e.g. methyl 6,6-dimethoxycaproate), undergoes cleavage to give the corresponding vinyl ether and methanol, and the vinyl ether is hydrogenated to the saturated ether. These ethers have substantially lower boiling points than the acetals, and can therefore be separated off by distillation. The aldehyde (e.g. methyl 5-formylvalerate), which is likewise an important impurity in terms of amount, undergoes an aldol reaction at the acidic centers to give the corresponding aldol, which has a high molecular weight, and hence a substantially higher boiling point than the aldehyde or the carboxylate. The other troublesome impurities, such as monounsaturated or polyunsaturated compounds, are converted either to useful products or to compounds which can be separated off by distillation. In the case of the butenedicarboxylate, the hydrogenation carried out during the purification process gives methyl adipate. The unsaturated ketones are converted to saturated ones which can be easily separated off by distillation. The process is carried out at elevated temperatures, preferably from 50° to 300° C., in particular from 100° to 150° C. Where acidic ion exchangers doped with the stated metals are used, it has been found to be particularly useful if the temperature is maintained at from 80° to 140° C.

The hydrogenation with hydrogen can be carried out under atmospheric pressure, but, because of the increased hydrogen solubility, it has been found to be advantageous to maintain superatmospheric pressure, for example not more than 10 bar. In the subsequent distillation, the carboxylates have only to be separated off from components which have substantially higher or lower boiling points. It should be particularly emphasized that this distillation does not make any especially high demands with respect to the number of separation stages.

The process is advantageous firstly because carboxylates can be freed from several types of impurities at the same time by a simple procedure, and can be obtained in a very pure form, so that very expensive separation processes which are otherwise required can be dispensed with. These would otherwise be absolutely necessary in order to ensure that the dicarboxylic acids prepared from these products were of textile-grade quality. Thus, the technical complexity of the preparation of pure carboxylates is greatly reduced by the novel purification process.

Secondly, the use, according to the invention, of a catalyst possessing acidic centers, for example a zeolite or strongly acidic ion exchanger which is doped with one or more metals of group VIII of the periodic table, ensures that only undesirable compounds, and not the ester functions of the desired product, are attacked. In contrast, if a conventional industrial hydrogenation were carried out using a conventional catalyst without the above double function, even under mild conditions the ester function would be hydrogenated to produce ester-alcohols (e.g. methyl 6-hydroxycaproate), which, even under mild thermal conditions, undergo cyclization to lactones, e.g. ε-caprolactone, with elimination of methanol. Frequently, such lactones cannot be separated off from the desired product by distillation. This applies in particular to the preparation of dimethyl adipate, which in such a case would be unsuitable for the textile sector. Moreover, partial hydrogenation of ester functions must be regarded as a real loss of desired product. In contrast, the novel purification process is an elegant method for the purification of carboxylates which is easy to carry out technically and even gives additional small amounts of the desired product.

The esters purified according to the invention are useful as solvents. Adipates are hydrolyzed to adipic acid, which is a starting material for the preparation of polycondensates with nylon 6,6.

The Examples which follow illustrate the process according to the invention.

EXAMPLE 1

0.2 liter of a strongly acidic ion exchanger (crosslinked polystyrene possessing sulfonic acid groups) which is doped with 1.0% by weight of palladium, and 0.8 kg of dimethyl adipate which contains 0.3% by weight of methyl 6,6-dimethoxycaproate, 0.25% by weight of methyl 5-formylvalerate, 0.07% by weight of dimethyl butenedicarboxylate, 0.015% by weight of tridecenones and 0.2% by weight of dimethyl 2-methylglutarate and has an extinction coefficient of 20,260, are introduced into a 2 liter shaken autoclave. Hydrogen is forced in under a pressure of 5 bar, and the mixture is then heated for 2.5 hours at 125° C., the autoclave being shaken at the same time. The product obtained after cooling has a UV number of 2,800. Rectification gives 99.75% strength by weight dimethyl adipate which has a UV number of 1,900 and still contains 0.1% by weight of dimethyl 2-methylglutarate.

EXAMPLE 2

18 liters/hour of 99.2% strength by weight dimethyl adipate and 80 liters (S.T.P.)/hour of hydrogen are introduced into a 9 m tube reactor which contains 40 liters of a strongly acidic ion exchanger doped with 1.5 g of palladium per liter of dry ion exchanger. The reactor is operated in a flooded state, and kept at 110° C. and under a pressure of 8 bar. The ester employed contains on average 0.5% by weight of methyl 6,6-dimethoxycaproate, 0.13% by weight of methyl 5-formylvalerate, 0.02% by weight of dimethyl butenedicarboxylate, 0.02% by weight of tridecenones and tetradecenones and 0.05% by weight of dimethyl 2-methylglutarate and has an average UV number of 14,000. The product from the reactor is fed to a distillation column having 30 theoretical plates, from which column the desired product is taken off as a sidestream. The dimethyl adipate obtained is 99.85% pure and has an average UV number of 1,200.

We claim:

1. A process for purifying a carboxylate which contains aldehydes, acetals and/or unsaturated compounds and is obtained by reacting an olefinically unsaturated compound with carbon monoxide and an alkanol which process comprises: treating said carboxylate with hydrogen at elevated temperatures in the presence of an acidic ion exchanger or zeolite doped with one or more metals of group VIII of the periodic table, and separating the resulting low and/or high boilers by distillation.

2. The process of claim 1, wherein the acidic ion exchanger or the zeolite is doped with palladium or platinum.

3. The process of claim 1, wherein the temperature employed is from 80° to 140° C.

4. The process of claim 1, wherein a strongly acidic ion exchanger is used.

5. The process of claim 1, wherein the starting mixture is dimethyl adipate containing, as impurities, methyl 5-formylvalerate and/or methyl 6,6-dimethoxycaproate and/or dimethyl butenedicarboxylate and/or tridecenones.

* * * * *